(12) United States Patent
Chang et al.

(10) Patent No.: US 11,578,049 B2
(45) Date of Patent: Feb. 14, 2023

(54) BENZOIC ACID COMPOUND AND METHOD FOR PREPARING THE SAME

(71) Applicant: Henan Genuine Biotech Co., Ltd., Pingdingshan (CN)

(72) Inventors: Junbiao Chang, Zhengzhou (CN); Jinfa Du, Zhengzhou (CN); Kaikai Zhu, Zhengzhou (CN); Kai Wang, Zhengzhou (CN)

(73) Assignee: HENAN GENUINE BIOTECH CO., LTD., Pingdingshan (CN)

(*) Notice: Subject to any disclaimer, the term of this patent is extended or adjusted under 35 U.S.C. 154(b) by 162 days.

(21) Appl. No.: 17/026,339

(22) Filed: Sep. 21, 2020

(65) Prior Publication Data

US 2021/0002244 A1    Jan. 7, 2021

Related U.S. Application Data

(63) Continuation-in-part of application No. PCT/CN2019/078059, filed on Mar. 14, 2019.

(30) Foreign Application Priority Data

Mar. 19, 2018 (CN) .......................... 201810225467.4

(51) Int. Cl.
| | | |
|---|---|---|
| C07D 307/83 | (2006.01) | |
| A61P 25/00 | (2006.01) | |
| C07C 69/78 | (2006.01) | |
| C07D 307/88 | (2006.01) | |
| C07C 67/307 | (2006.01) | |
| C07C 67/343 | (2006.01) | |

(52) U.S. Cl.
CPC ............. *C07D 307/83* (2013.01); *A61P 25/00* (2018.01); *C07C 67/307* (2013.01); *C07C 67/343* (2013.01); *C07C 69/78* (2013.01)

(58) Field of Classification Search
CPC ....... C07C 69/78; A61P 25/00; C07D 307/83; C07D 307/88
See application file for complete search history.

(56) References Cited

FOREIGN PATENT DOCUMENTS

| CN | 101029037 A | * | 9/2007 |
|---|---|---|---|
| CN | 101402565 A | * | 4/2009 |

OTHER PUBLICATIONS

Translation of the claims of the Chinese Patent Publication CN-101029037-A. (Year: 2022).*
Translation of the description of the Chinese Patent Publication CN-101029037-A. (Year: 2022).*
English translation of the description of Chinese Publication CN-101402565-A (Year: 2022).*
English translation of the claims of Chinese Publication CN-101402565-A (Year: 2022).*

* cited by examiner

*Primary Examiner* — Joseph R Kosack
*Assistant Examiner* — Sagar Patel
(74) *Attorney, Agent, or Firm* — Matthias Scholl P.C.; Matthias Scholl

(57) ABSTRACT

A compound represented by formula I or II. X represents a mono substituent on a benzene ring, and is selected from —H, —I, —Br, —Cl, —F, —CN, an amino, and a derivative thereof; $R_1$ is a $C_{2-10}$ alkyl, $C_{2-10}$ alkyl substituted by cyclopropane or fluorine, except n-butyl; and M is an amine ion or metal ion.

8 Claims, 1 Drawing Sheet

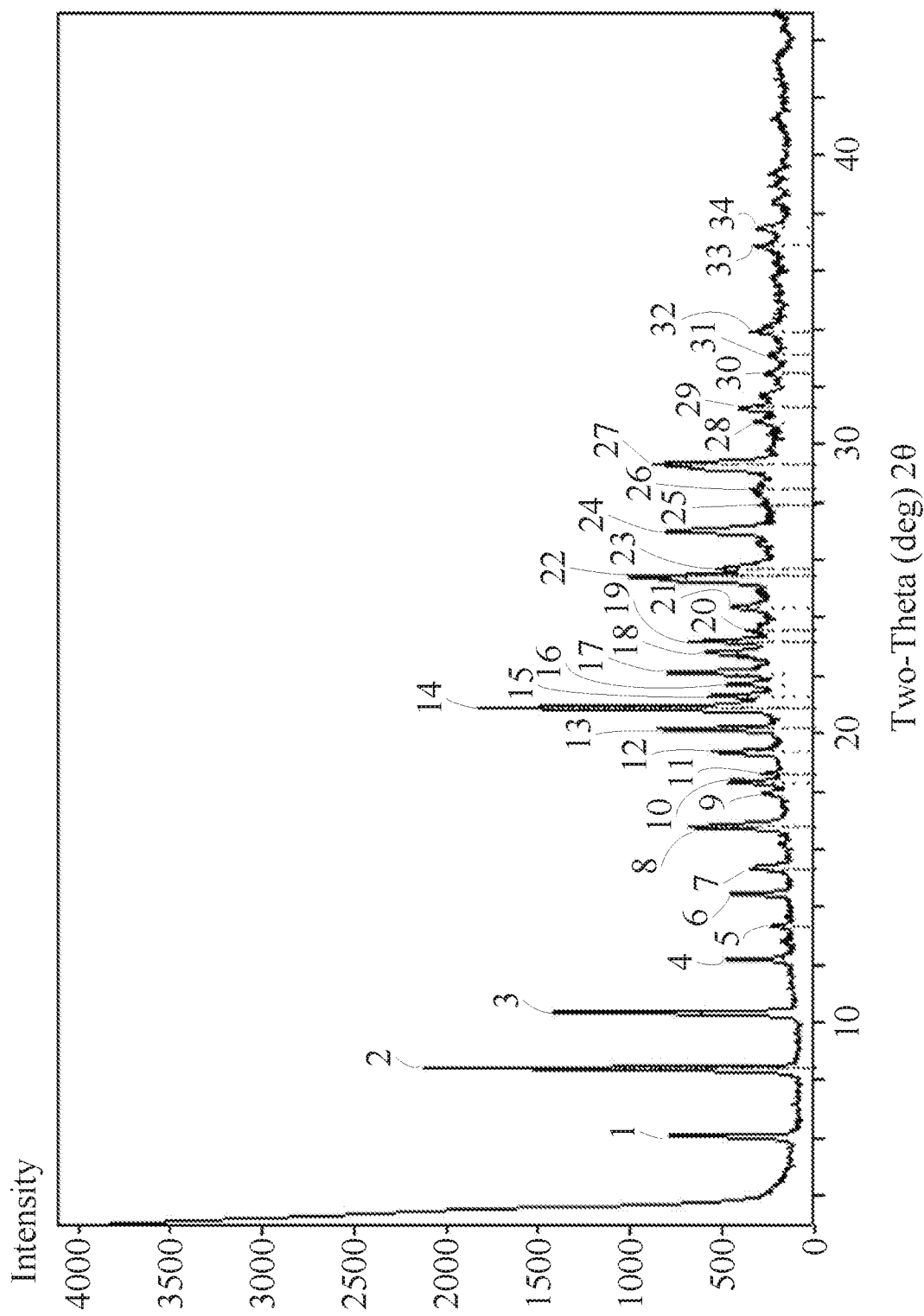

BENZOIC ACID COMPOUND AND METHOD FOR PREPARING THE SAME

CROSS-REFERENCE TO RELATED APPLICATIONS

This application is a continuation-in-part of International Patent Application No. PCT/CN2019/078059 with an international filing date of Mar. 14, 2019, designating the United States, now pending, and further claims foreign priority benefits to Chinese Patent Application No. 201810225467.4 filed on Mar. 19, 2018. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND

The disclosure relates to a benzoic acid compound, its application thereof in the prevention and treatment or relief of ischemic diseases such as cerebral ischemia or acute or chronic myocardial infarction, and also relates to the application of the benzoic acid compound in the prevention and treatment or relief of amyotrophic lateral sclerosis (ALS). The disclosure relates to the field of pharmaceutical chemistry.

Cardiovascular and cerebrovascular diseases, especially coronary atherosclerosis and the associated ischemic heart and brain diseases, are common diseases that seriously damages human health. Butylphthalide is a drug approved for the treatment of stroke. Benzylpiperazine (BZP) (structural formula A) is in clinical trials. The metabolism of butylphthalide shows that the two carbon at the ends of the side chain are easily oxidized by cytochrome P450, and the proportion of the metabolites of butylphthalide in human body is as follows. The total metabolites M3-2, M2, M5-2 of adults after oral administration of 200 mg of butylphthalide are 16 times higher than that of the effective drug n-butylphthalide (NBP).

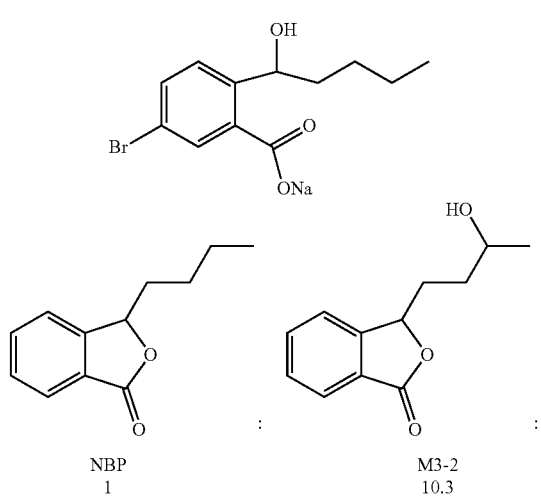

NBP
1

M3-2
10.3

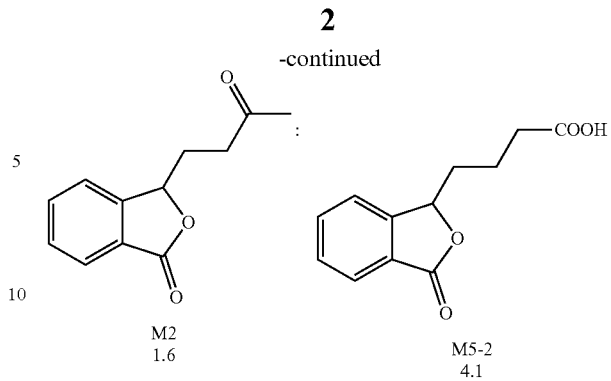

M2
1.6

M5-2
4.1

SUMMARY

One objective of the disclosure is to provide a benzoic acid compounds by modifying the terminal of p-butylphthalide and BZP for treating cerebral infarction, myocardial ischemic, amyotrophic lateral sclerosis and other diseases. Deuterated analogues and prodrugs thereof are also included in the scope of the disclosure.

To achieve the objective of the disclosure, the terminal of p-butylphthalide and BZP is modified, and a series of novel BZP derivatives are synthesized.

The disclosure provides a compound being represented by formula I or II:

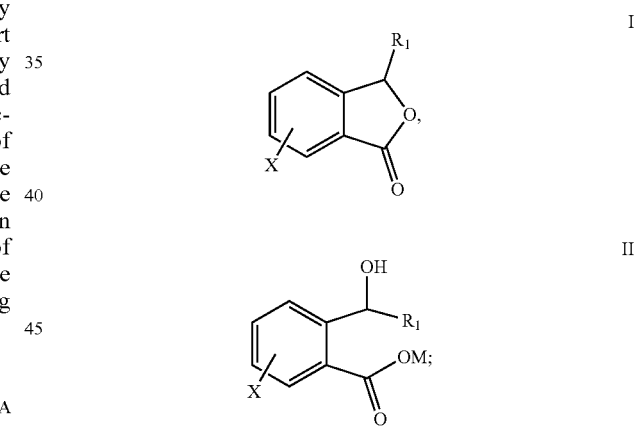

X represents a mono substituent on a benzene ring, and is selected from —H, —I, —Br, —Cl, —F, —CN, an amino, and a derivative thereof;

$R_1$ is a $C_{2-10}$ alkyl, $C_{2-10}$ alkyl substituted by cyclopropane or fluorine, except n-butyl; and M is an amine ion or metal ion.

In a class of this embodiment, X represents a mono substituent on a benzene ring, and is selected from —H, —I, —Br, —Cl, —F, —CN, an amino, and a derivative thereof; $R_1$ is a $C_{3-5}$ alkyl, $C_{3-5}$ alkyl substituted by cyclopropane or fluorine, except n-butyl; and M is an ion of K, Na, Ca, Zn or Mg.

In a class of this embodiment, X is Br or F; $R_1$ is a $C_{3-5}$ alkyl, $C_{3-5}$ alkyl substituted by cyclopropane or fluorine, except n-butyl; and M is an ion of K, Na, Ca.

In a class of this embodiment, R₁ has one of the following structural formula:

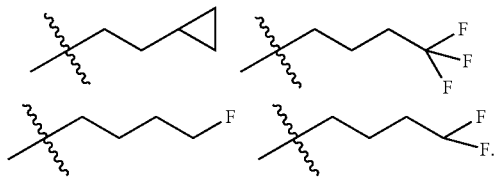

In a class of this embodiment, the compound has one of the following structural formulas:

III
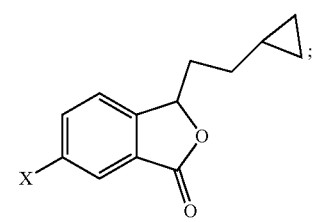

IV
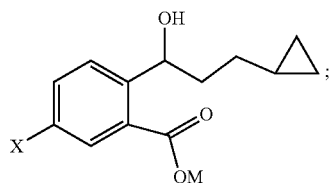

V
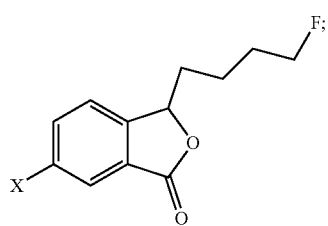

VI
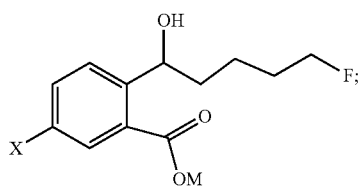

VII
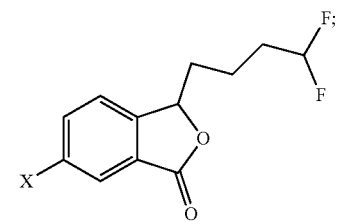

VIII
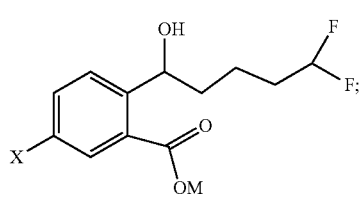

IX
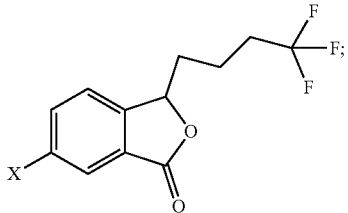

IX
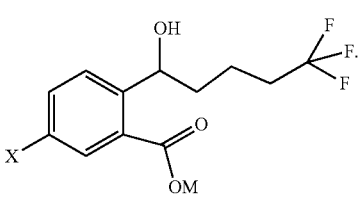

The disclosure further provides the compounds I-X for use as a medicament for prevention, treatment and relief of cerebral ischemia.

The disclosure also provides the compounds I-X for use as a medicament for prevention, treatment and relief of acute or chronic myocardial ischemia.

The disclosure still provides the compounds I-X for use as a medicament for prevention, treatment and relief of amyotrophic lateral sclerosis.

Deuterated analogues of the compounds I-X are also included in the scope of the disclosure.

The preparation method of the compounds I-X is described as follows:

Compound 1 is brominated with NBS in the presence of AIBN (azodiisobutyronitrile) to yield a compound 2. Without purification, the compound 2 is heated and hydrolyzed in water to form a compound 3:

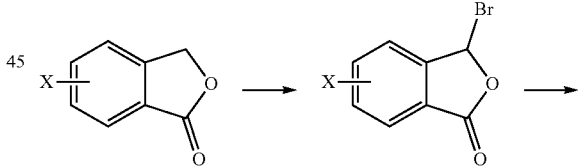

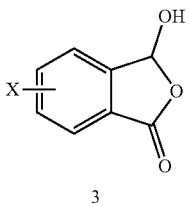

The Compound 3 reacts with a Grignard reagent to yield a lactone 4, which is hydrolyzed in an alkali to yield a salt 5:

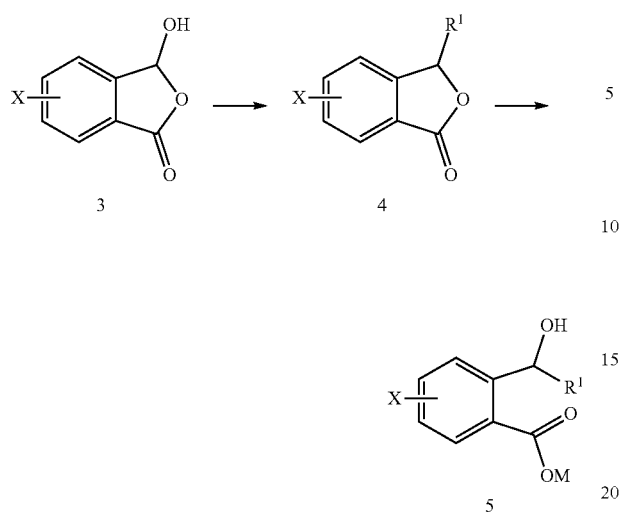

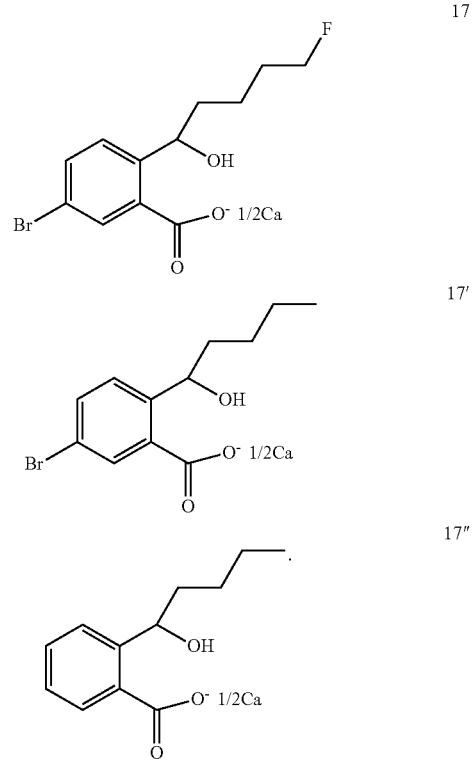

The following advantages are associated with the benzoic acid compounds of the disclosure:

1. The animal experiment results show that the novel compounds synthesized in the disclosure has obvious protective effect on the cerebral ischemia-reperfusion injury. Both BZP and the compounds 14-16 exhibit significant effects on the recovery of cerebral blood flow after cerebral ischemia-reperfusion; especially, the compound 15 (95.6% of the preoperative recovery) is more effective than BZP. In particular, the inhibitory effect of the compound 15 on the formation of cerebral infarction area after cerebral ischemic. was 75.3%, which is three times that of butylphthalide potassium (26.4%).

2. In vitro stability test of human liver microsomes shows that the half-life (T½) of compound 15 is 19.09 hours, which is longer than 4.17 hours of BZP and less than 1 hour of butylphthalide potassium.

3. The results of acute toxicity test in mice show that the toxicity of the compound 15 is significantly lower than that of potassium butylphthalide and BZP. The median lethal dose of the compound 15 is 1036 mg, which is much higher than that of 373 mg of potassium butylphthalide and 330 mg of BZP.

4. The compound 15 and its calcium salt 17 have similar efficacy, biological stability and toxicity.

5. The type of the salt of the compound 5 affects its physical properties. The sodium salt of the compound 15 is difficult to crystallize and is easy to absorb water in the air, Moreover, the excess alkali (NaOH) cannot be removed, which affects the purity of the product. In addition, the excess alkali leads to the closed-loop reaction between hydroxyl group and fluorine atom. Potassium hydroxide contacts the compound 12 to yield a potassium salt which is not a solid. The calcium salt of the compound 17 is easy to crystallize and precipitate from aqueous solution, which has the characteristics of easy preparation, no water absorption and suitable for large-scale production. Therefore, high-purity of potassium salt and sodium salt products are not easy to obtain in this disclosure, which is unfavorable to large-scale production. Therefore, the following compounds are also included in the present invention:

The compound of the disclosure is expected to be used for the development of drugs for treating cerebral infarction, myocardial ischemia diseases, and amyotrophic lateral sclerosis.

BRIEF DESCRIPTION OF THE DRAWINGS

The invention is described hereinbelow with reference to accompanying drawings, in which the sole FIGURE is an X-ray powder diffraction (XRPD) pattern of the crystal form A of a compound 17 according to one embodiment of the disclosure.

DETAILED DESCRIPTION

To further illustrate, embodiments detailing a benzoic acid compound and preparation method thereof are described below. It should be noted that the following embodiments are intended to describe and not to limit the disclosure.

EXAMPLE 1

Preparation of Compound 8

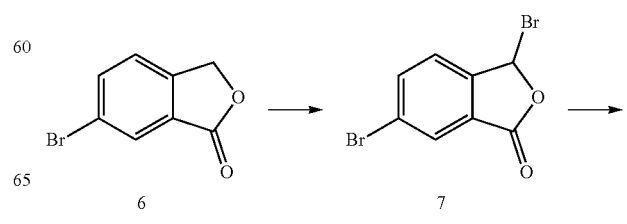

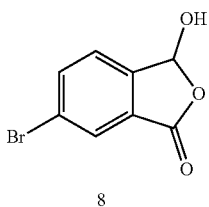

8

The compound 6 (2.0 g, 9.39 mmol), N-bromosuccinimide (NBS) (1.84 g, 1.5 azodiisobutyronitrile (AIBN) (154 mg, 0.94 mmol) were added to carbon tetrachloride (30 mL). The mixture was refluxed for 2 h, cooled to room temperature and filtered. The solvent was evaporated to yield compound 7, followed by addition of water (10 mL). The mixture was heated at reflux for 1 hour, cooled to room temperature, and extracted with EtOAc (200 mL). The combined organic extracts were washed with saturated brine, dried over Na$_2$SO$_4$, filtered and evaporated to yield compound 8 (2.05 g, 95% yield).

EXAMPLE 2

Preparation of Compound 10

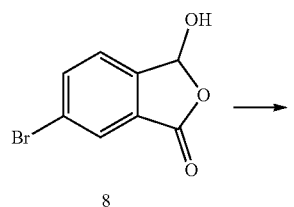
8

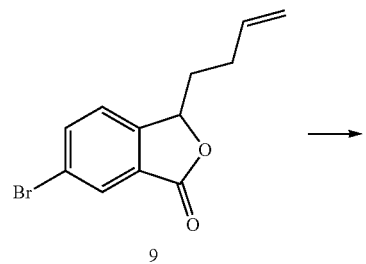
9

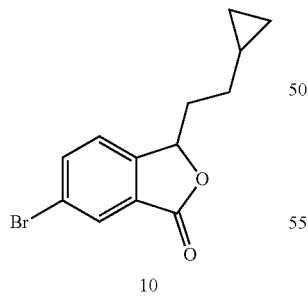
10

To a three-neck round bottom flask, magnesium bar (0.63 g, 26.22 mmol), dry tetrahydrofuran (THF, 20 mL), and iodine were added. To the mixture under nitrogen at 50° C., a solution of 4-bromo-1-butene (2.95 g, 21.83 mmol) in THF (2 mL) slowly dropwise was added. The reaction mixture was heated to reflux for 2 hours, thereby producing Grignard reagent. To the compound 8 in THF (10 mL) under nitrogen at 0° C., was then added freshly prepared Grignard reagent dropwise. The mixture was stirred at room temperature for 2 hours at 0° C., quenched with 1N HCl, heated to evaporate THF, diluted with DCM (Dichloromethane) and acidified to pH 2.0 with 1N HCl. The reaction was conducted at room temperature overnight. The resulting solution was diluted with EtOAc (100 mL). The phases were separated and the organic phase was dried over Na$_2$SO$_4$, filtered and evaporated. The residue was purified by silica gel column to yield compound 9 as a white solid (325 mg, 28% yield).

$^1$H NMR (400 MHz, CDCl$_3$) δ 8.05 (d, J=1.71 Hz, 1H), 7.81 (dd, J=8.1, 1.8 Hz, 1H), 7.35 (d, J=8.1 Hz, 1H), 5.84 (ddt, J=17.0, 10.2, 6.6 Hz, 1H), 5.48 (dd, J=8.3, 3.7 Hz, 1H), 5.15-5.01 (m, 2H), 2.37-2.20 (m, 2H), 2.18-2.07 (m, 1H) 1.86 (dtd, J=14.2, 8.5, 5.4 Hz, 1H); m/z (ES+) (M+H)$^+$=268.

To dry DCM (5 mL) in a three-neck round bottom flask under nitrogen, 1.0 M diethylzinc in n-hexane solution (2.4 mL, 2.4 mmol) was added. After cooling down to −10° C., a solution of trifluoroacetic acid (277 mg, 2.4 mmol) in DCM (5 mL) was added and the reaction mixture was stirred for 20 min. A solution of diiodomethane (652 mg, 2.4 mmol) in DCM (5 mL) was added dropwise in the resulting solution and the mixture was stirred for 2 to 3 hours. Then the mixture was quenched by adding a saturated solution of aqueous chloride dropwise at 0° C., and diluted with EtOAc. The phases were separated and the organic phase was dried over Na$_2$SO$_4$, filtered and evaporated. The residue was purified by silica gel column to yield compound 10 as a white solid (45 mg, 86% yield).

$^1$H NMR (400 MHz, CDCl$_3$) δ 8.04 (d, J=1.3 Hz, 1H), 7.80 (dd, J=8.1, 1.7 Hz, 1H), 7.35 (d, J=8.1 Hz, 1H), 5.53 (dd, J=8.2. 3.9 Hz, 1H), 2.23-2.11 (m, 1H), 1.86 (dtd, J=14.3, 8.5, 5.6 Hz, 1H), 1.47-1.31 (m, 2H), 0.78-0.63 (m, 1H), 0.54-0.39 (m, 2H), 0.18-0.03 (m, 2H); m/z (ES+) (M+H)$^+$=282.

EXAMPLE 3

Preparation of Compound 12

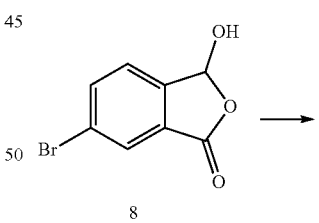
8

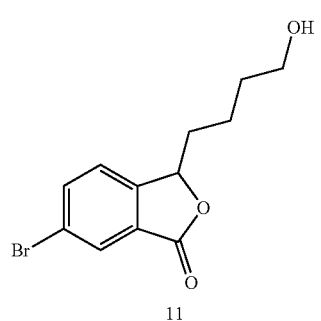
11

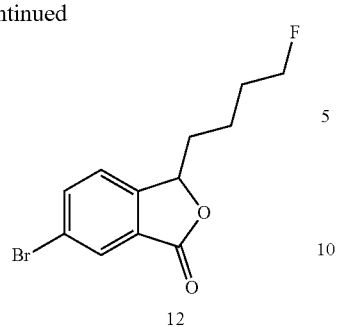

12

To a three-neck round bottom flask, magnesium bar (125 mg, 5.22 mmol), dry THF (5 mL), and iodine were added. To the mixture under nitrogen and heated conditions, a solution of (4-bromobutoxy)(tert-butyl)dimethylsilane (1.16 g, 4.35 mmol) in THF (4 mL) slowly dropwise was added. The reaction mixture was heated to reflux for 2 hours, thereby producing Grignard reagent. To the compound 8 in THF (10 mL) under nitrogen at 0° C., was then added freshly prepared Grignard reagent dropwise. The mixture was stirred at room temperature for 2 hours, quenched with 1N HCl at 0° C., heated to evaporate THF, diluted with DCM (50 mL) and acidified to pH 2.0 with 1N HCl. The reaction was conducted at room temperature overnight. The resulting solution was diluted with EtOAc (100 mL). The phases were separated and the organic phase was dried over Na$_2$SO$_4$, filtered and evaporated. The residue was purified by silica gel column to yield compound 11 as a white solid (45 mg, 18% yield).

$^1$H NMR (400 MHz, CDCl$_3$) δ 8.02 (d, J=1.7 Hz, 1H), 7.78 (dd, J=8.1, 1.8 Hz, 1H), 7.33 (d, J=8.1 Hz, 1H), 5.45 (dd, J=7.8, 4.0 Hz, 1H), 3.68-3.62 (m, 2H), 2.54 (s, 1H), 2.15-2.05 (m, 1H), 1.84-1.72 (m, 1H), 1.69-1.46 (m, 4H).

The compound 11 was diluted in DCM (3 mL) and cooled to −78° C. To the mixture under nitrogen, a solution of DAST (diethylaminosulfur trifluoride) (77 mg, 0.48 mmol) in DCM (3 mL) was added. After stirring at room temperature for 2 hours and addition of water, the resulting mixture was quenched, extracted and extracted. The phases were separated and the organic phase was dried over Na$_2$SO$_4$, filtered and evaporated. The residue was purified by silica gel column to yield compound 12 as a white solid (26 mg, 58% yield).

$^1$H NMR (400 MHz, CDCl$_3$) δ 8.05 (d, J=1.6 Hz, 1H), 7.82 (dd, J=8.1, 1.7 Hz, 1H), 7.35 (d, J=8.1 Hz, 1H), 5.48 (dd, J=7.9, 3.9 Hz, 1H), 4.53 (tt, J=5.4, 2.7 Hz, 1H), 4.42 (tt, J=5.4, 2.7 Hz, 1H), 2.18-2.06 (m, 1H), 1.85-1.71 (m, 3H), 1.69-1.59 (m, 2H). $^{19}$F NMR (376 MHz, DMSO) δ −218.60. m/z (ES+) (M-H)$^+$=286.

EXAMPLE 4

Preparation of Compound 13

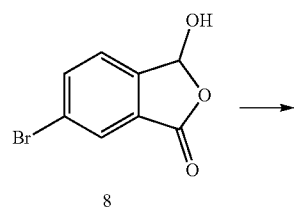

8

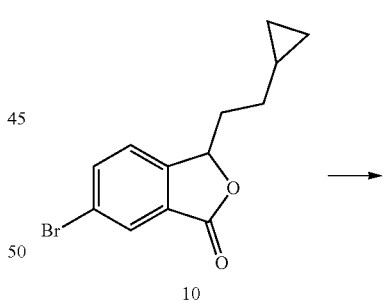

13

To a three-neck round bottom flask, were added magnesium bar (151 g, 6.29 mmol), dry THF (5 mL), and iodine. To the mixture under nitrogen and heated conditions, a solution of 1-bromo-4,4,4-trifluorobutane (1.0 g, 5.24 mmol) in THF (2 mL) slowly dropwise was added. The reaction mixture was heated to reflux for 2 hours, thereby producing Grignard reagent. To the compound 8 (240 mg, 1.05 mmol) in THF (5 mL) under nitrogen at 0° C., was then added freshly prepared Grignard reagent dropwise. The mixture was stirred at room temperature for 2 hours, quenched with 1N HCl at 0° C., heated to evaporate THF, diluted with DCM (20 mL) and acidified to pH 2.0 with 1N HCl. The reaction was conducted at room temperature overnight, and the resulting solution was diluted with EtOAc (100 mL). The phases were separated and the organic phase was dried over Na$_2$SO$_4$, filtered and evaporated. The residue was purified by silica gel column to yield compound 13 as a white solid (110 mg, 33% yield).

$^1$H NMR (400 MHz, CDCl$_3$) δ 8.06 (s, 1H), 7.83 (dd, J=8.1, 1.7 Hz, 1H), 7.35 (d, J=8.1 Hz, 1H), 5.47 (dd, J=7.2, 3.6 Hz, 1H), 2.26-2.14 (m, 3H), 1.87-1.73 (m, 3H). $^{19}$F NMR (376 MHz, DMSO) δ −66.12. m/z (ES+) (M+H)$^+$=324.

EXAMPLE 5

Preparation of Compound 14

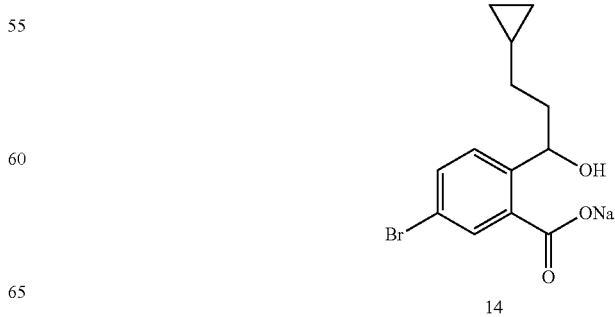

To the compound 8 (30 mg, 0.11 mmol) dissolved in a mixed solution: MeOH/H$_2$O (4 mL, 1:1), NaOH (8.6 mg, 0.21 mmol) was added. After stirring at 50° C. for 5 hours, the solvent was evaporated and the residue was triturated several times with diethyl ether. The residue was triturated with diethyl ether and filtered. The filtrate was allowed to stand at 0° C. overnight. The resulting precipitate was collected to yield compound 14 as a white solid (19 mg, 59% yield).

$^1$H NMR (400 MHz, DMSO) δ 7.89 (d, J=7.4 Hz, 1H), 7.79 (s, 1H), 7.36 (d, J=7.8 Hz, 1H), 7.12 (d, J=8.1 Hz, 1), 4.54 (d, J=5.9 Hz, 1H), 1.87-1.61 (m, 2H), 1.23 (s, 1H), 1.11-0.97 (m, 1H), 0.63 (s, 1H), 0.33 (d, J=7.3 Hz, 2H), −0.06 (s, 2H); m/z (ES+) (M-Na)$^-$=297.

EXAMPLE 6

Preparation of Compound 15

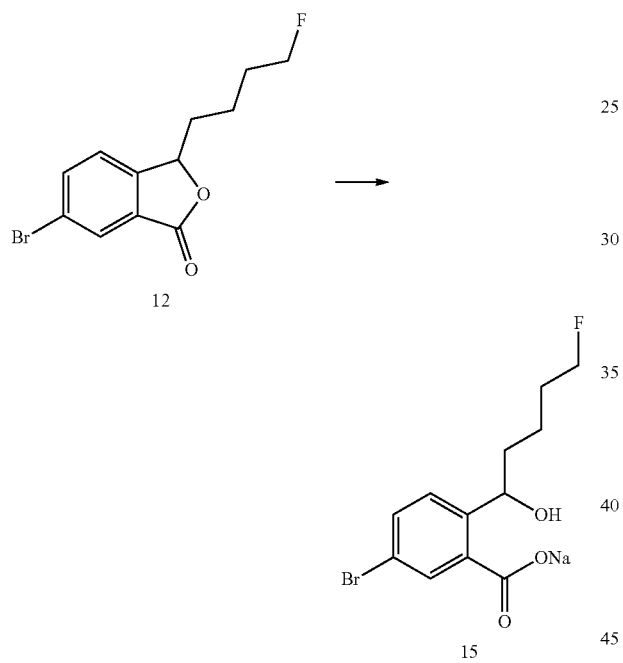

To the compound 12 (93 mg, 0.33 mmol) dissolved in mixed solution: MeOH/H$_2$O (11 mL, 1:1), NaOH (26 mg, 0.65 mmol) was added. After stirring at 50° C. for 5 hours, the solvent was evaporated and the residue was triturated several times with diethyl ether to yield compound 15 as a white solid (93 mg, 95% yield).

$^1$H NMR (400 MHz, DMSO) δ 8.12 (d, J=8.0 Hz, 1H), 7.77 (s, 1H), 7.35 (d, J=8.1 Hz, 1H), 7.12 (d, J=8.1 Hz, 1H), 4.57-4.40 (m, 2H), 4.35 (dd, J=14.9, 8.9 Hz, 1H), 1.69-1.53 (m, 4H), 1.49-1.35 (m, 1.22 (d, J=9.5 Hz, 1H); $^{19}$F NMR (376 MHz, DMSO) δ −216.41. m/z (ES+) (M-Na)$^-$=303.

EXAMPLE 7

Preparation of Compound 16

To the compound 13 (100 mg, 0.31 mmol) dissolved in mixed solution: MeOH/H$_2$O (10 mL, 1:1), was added NaOH (25 mg, 0.62 mmol). After stirring at 50° C. for 5 hours, the solvent was evaporated and the residue was triturated several times with diethyl ether. The residue was triturated with diethyl ether and filtered. The filtrate was allowed to stand at a low temperature overnight. The resulting precipitate was collected to yield compound 16 as a white solid (50 mg, 44% yield).

m/z (ES+) (M-Na)$^-$=339.

EXAMPLE 8

Preparation of Compound 17

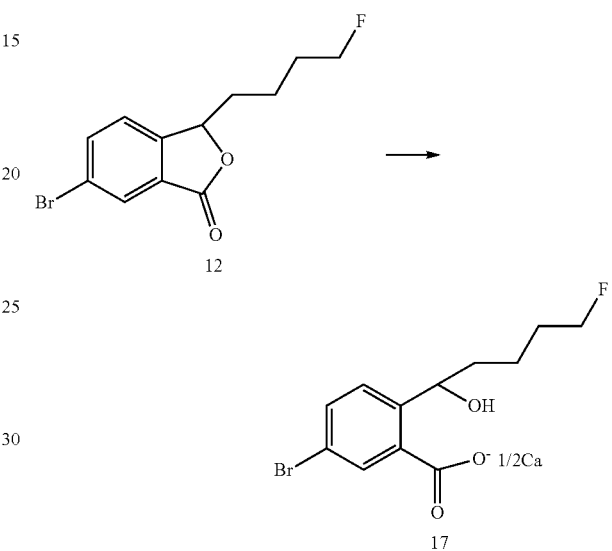

To the compound 12 (5.0 g, 17.4 mmol, 1.0 eq) dissolved in 50 mL of methanol, was added NaOH (870.7 mg, 20.9 mmol, 1.2 eq). After stirring at 70° C. for 4 hours, the mixture was rotated to be spin-dried to yield sodium salt as a white solid. After addition of water (50 mL), the mixture was basified to pH 7-8 with 1 M acetic acid (HOAc). To the basified mixture at 60° C., was added dropwise a solution of calcium acetate monohydrate (1.57 g, 8.7 mmol, 0.5 eq) dissolved in water (25 mL) until solid precipitated. The mixture was stirred for 20 min, followed by an addition of the residue solution dropwise. After stirring for 1 h and cooling to room temperature, the mixture was filtered, washed with water, ethanol and ether, and dried under vacuum to yield compound 7 as a white solid (5.32 g, 97% yield).

$^1$NMR (400 MHz, DMSO) δ 7.88 (d, J=1.9 Hz, 2H), 7.44 (dd, J=8.2, 2.2 Hz, 2H), 7.28 (d, J=8.2 Hz, 2H), 6.88 s, 4.89 (s, 2H), 4.44 (t, J=6.0 Hz, 2H), 4.32 (t, J=6.0 Hz, 2H), 1.69-1.54 (m, 8H), 1.49-1.39 (m, 2H), 1.33-1.22 (m, 2H); $^{19}$F NMR (376 MHz, DMSO) δ −216.3; m/z (ESi) (M-Na)$^-$=303.

Form A is the most stable crystal form of the compound 17. Form A has an X-ray powder diffraction (XRPD) pattern measured using an incident beam of Cu-Kα radiation of wavelength λ=1.5418 Å comprising following 2θ peaks (average 2θ in (°) are indicated with error limit of ±0.2): 2θ in (°): 6.10, 8.43, 10.36, 12.18, 13.34, 14.46, 15.30, 16.77, 17.93, 18.31, 18.60, 19.36, 20.16, 20.88, 21.30, 21.70, 22.10, 22.81, 23.18, 23.57, 24.37 (as shown in the sole figure).

Relative intensity of the stable crystal form A of compound 17 at different diffraction angles 2θ:

| 2θ (±0.2°) | Relative intensity I % |
|---|---|
| 6.10 | 33.0 |
| 8.42 | 100 |
| 10.36 | 64.9 |
| 12.18 | 17.5 |
| 16.77 | 26.2 |
| 19.36 | 17.9 |
| 19.36 | 17.9 |
| 20.16 | 31.5 |
| 20.88 | 77.7 |
| 22.10 | 26.4 |
| 23.18 | 20.6 |
| 25.45 | 36.6 |
| 26.99 | 27.6 |
| 29.30 | 31.1 |

EXAMPLE 9

Pharmacodynamic Study

Materials and Methods

1. Experimental Procedure 1.1 Animal adaptions: Animals were housed in a temperature (20-24° C.) and moisture-controlled (30-70%) room with a 12 h light-dark cycle (light on from 7:00 A.M. to 7:00 P.M.). The light-dark cycle was controlled by an electronic timed lighting system. The in-door temperature and humidity were measured in real-time with a thermometer-hygrometer, and recorded twice daily (once early in the morning and once late in the afternoon).

1.2 Experimental procedure: Male Sprague Dawley (SD) rats was subjected to operation after experimental adaption for 5-7 days, with a weight of 200-250 g. The rats were anesthetized by intraperitoneal injection of 0.35 mL/100 g 10% chloral hydrate, and positioned on a temperature-controlled, operating surface. The common carotid artery was isolated from surrounding nerves to the bifurication between the external carotid artery and the internal carotid artery. The external carotid artery was then isolated. A sterile middle cerebral artery occlusion (MCAO) suture was advanced through external carotid artery into the internal carotid artery (about 18 mm±0.5 mm from the point of the carotid bifurication), effectively occluding the middle cerebral artery. The suture was withdrawn after 2 hours ischemic period to simulate clinical reperfusion. All rats were scored according to Longa scoring system, in which the rats with a total score less than 1 were withdrawn. The rats were kept on a heating blanket and allowed to recover from anesthesia. A neurobehavioral examination was performed at 24 h after awakening. Blood was drawn from each rat under anesthesia, collected in a tube containing K2-EDTA as anticoagulant for stabilizing the blood samples, centrifuged to separate supernatant from precipitate, and stored at 80° C. Then the rats were euthanized. The brains were cut into slices, stained with 2,3,5-triphenyltetrazolium chloride (TTC), and used to determine the infarct area. The experiment was complete within 3 days, with 3-4 rats per group daily.

1.3 Intraoperative monitoring: Transcranial measurement of cerebral blood flow was made using laser dropper at three points, namely before the operation, immediately after the initiation of ischemia, and immediately after reperfusion.

1.4 Withdrawal criteria at the end of treatment: 1) No cerebral infarction; 2) Subarachnoid hemorrhage.

1.5 Daily monitoring: The rats were observed daily from the first day of housing, weighed and evaluated weekly for health assessment.

1.6 Grouping: 70 Rats were randomly divided into equal groups and each group contained 10 rats (Listed in Table below).

| Experiment | Group | Number | Dose | Administration method | Administration time |
|---|---|---|---|---|---|
| 1 | Sham-operated group | 10 | | iv | Immediately after reperfusion |
| 2 | Model group | 10 | | iv | Immediately after reperfusion |
| 3 | BZP | 10 | 3 mg/kg | iv | Immediately after reperfusion |
| 4 | Compound 14 | 10 | 3 mg/kg | iv | Immediately after reperfusion |
| 5 | Compound 15 | 10 | 3 mg/kg | iv | Immediately after reperfusion |
| 6 | Compound 16 | 10 | 3 mg/kg | iv | Immediately after reperfusion |
| 7 | Compound 17 | 10 | 3 mg/kg | iv | Immediately after reperfusion |

1.7 Drug preparation: The drugs to be tested were accurately weighed, dissolved in physiological saline to give a final concentration of 1.5 mg/mL.

1.8 Administration method: The drugs were removed from the refrigerator and cooled to room temperature before the rats were dosed. The dosing volume was 2 mL/kg.

1.9 Experiments at the ending point of the treatment:

1.9.1 Neurobehavioral scoring: A neurobehavioral examination, according to modified Longa scoring system, was implemented at 24 h after reperfusion. Scoring was as follows: 0: normal, no observable neurologic deficit; 1: failure to extend contralateral (left) forepaw fully, a mild focal neurologic deficit; 2: moderately circling toward the left (paretic side), 3: severely circling to the left (paretic side); 4: falling to the left (paretic side); 5: no spontaneous gait, but have depressed level of consciousness.

1.9.2 Cerebral infarction ratio: The rats were euthanized with chloral hydrate (330 mg/kg anesthesia), given by $CO_2$ inhalation, and blood was drawn by cardiac puncture. The brains were removed from the skull and cut into 2 mm coronal slices using a rat brain matrix. Each slice was stained with 1% TTC at 37° C. for 5 minutes, protected from light, and were photographed. The ratio of infarct area was then determined using an image analysis software Image Pro Plus 6.0. The infarct areas were summed and divided by total brain area to yield the ratio of infarct area.

1.9.3 The plasma was collected for further testing and stored at −80° C.

2. Data Analysis

All data was imported into an Excel worksheet, and expressed as mean±standard error of the mean. Statistical significance was determined by one-way ANOVA with Dunnett's multiple comparison test (*$P<0.05$, **$P<0.01$).

Experimental Results

TABLE 1

Effect of drugs on cerebral blood flow in rats exposed to cerebral ischemia and reperfusion

| | Experiment | Postoperative/ Preoperative | Reperfusion/ Postoperative |
|---|---|---|---|
| Sham-operated group | 1 | 95.7% | |
| Model group | 2 | 16.2% | 83.6% |
| BZP | 3 | 15.2% | 91.1% |
| Compound 14 | 4 | 13.5% | 88.3% |
| Compound 15 | 5 | 16.8% | 95.6% |
| Compound 16 | 6 | 14.3% | 89.8% |
| Compound 17 | 7 | 15.5% | 95.3% |

The cerebral blood flow was decreased by more than 70% following middle cerebral artery occlusion in rats, and reperfusion was achieved (transient MCAO, also called tMCAO model) when the suture was removed after a certain interval. The results shown in Table 1 suggest that BZP and the compounds 14-16 have a significant effect on the recovery of cerebral blood flow after cerebral ischemia and reperfusion. In particular, the compounds 15 and 17 (recovered to 95.6% before surgery) had a more obvious effect on restoring cerebral blood flow than BZP (91.1%).

TABLE 2

Effect of drugs on infarct area of rats exposed to cerebral ischemia and reperfusion

| | Experiment | Cerebral infarction ratio | Percentage inhibition of cerebral infarction |
|---|---|---|---|
| Sham-operated group | 1 | 0% | |
| Model group | 2 | 52.2% | 0% |
| Potassium butylphthalide | 3 | 37.5% | 26.4% |
| BZP | 4 | 20.6% | 57.5% |
| Compound 15 | 5 | 12.0% | 75.3% |
| Compound 17 | 6 | 11.8% | 77.4% |

The results shown in Table 2 suggest that the cerebral infarction ratio reaches 52.2% in the tMCAO model without drug treatment, while exhibiting significant reduction in the tMCAO model dosed with BZP and the compound 15. In particular, the compound 15 has the most significant reduction in cerebral infarction area of rats with cerebral ischemia reperfusion, which is reduced to 12.0% lower than the potassium butylphthalide of 37.5% and BZP of 20.2%. The compound 17 is a calcium salt that has a similar effect of reducing the cerebral infarction area in the rats subjected to the cerebral ischemia and reperfusion as the calcium compound 15.

The results in Example 9 show that BZP and compounds 14-16 were adapted to improve the symptom of brain damage caused by tMCAO, and the use of the compound 15 leads to better outcomes comparable to the compound 17.

Referring to Table 1, compound 15 restores 95.3% of blood flow and 91.1% of BZP. Referring to Table 2, the compound 15 reduces the area of cerebral infarction to 12.0%, while BZP only reduced to 20.2%, and the worst case of potassium butylphthalide was 37.5%. In conclusion, the compound 15 has better effect on restoring cerebral blood flow and reducing the area of cerebral infarction than BZP and potassium butylphthalide.

Compound 17 is a calcium salt of the compound 15, and both have equivalent efficacy.

EXAMPLE 10

Stability in Human Microsomes

1. Experimental Materials 1.1 Experimental Reagents

BZP and compound 15 were obtained from Henan Meitaibao biopharmaceutical Co., Ltd., with a purity of higher than 97%;

Internal standard solution PHPB;

Potassium dihydrogen phosphate and dipotassium hydrogen phosphate, Analytical grade, were obtained from Sangon Biological Engineering Technology & Services (Shanghai) Co, Ltd.;

Human liver microsomes (HLM) were obtained from Research Institute for Liver Disease (Shanghai) Co., Ltd.;

Methanol, ICP-Mass Pure Grade, was obtained from Fisher Company;

Ammonium acetate, Analytical grade, was obtained from Sinopharm Chemical Reagent Co., Ltd.

1.2 Equipment

ACCELA liquid chromatography system, Thermo Company, USA;

TSQ Quantum Ultra mass spectrometry system, Thermo Company, USA.

2. Experimental Methods 2.1 Sample Preparation

To 50 μL of human liver microsomes in a tube, was added 50 μL of internal standard solution and 150 μL of methanol. The tube was vortexed on a vortex mixer for 30 seconds to mix contents, followed by centrifugation at 13,000 r/min for 5 min. Supernatant was aspirated and sterile filtered through a 0.22 μM membrane. 10 μL of filtrate was analyzed for LC/MS/MS analysis.

2.2 Metabolic Stability Measured in Human Liver Microsomes

1000 μL of a reaction system contained butylphthalide compounds (2 μg/mL), human liver microsomes (1.0 mg/ml), NADPH (2 mM) and phosphate buffer (100 mM, pH=7.4). Methanol concentration does not exceed 0.1% (v/v). The human liver microsomes were pre-incubated with MTB compound series for 5 min at 37° C. water bath in a phosphate buffer. The reaction mixture was initiated by an addition of NADPH and incubated for 0, 5, 10, 20, 30, 40, 60 and 120 minutes. To the resulting mixture cooled in an ice bath, was added 50 μL of internal standard solution and 150 μL of frozen methanol to terminate the reaction, then followed by LC/MS/MS detection with reference to 2.1).

2.3 Data Analysis

The concentrations of the MTB compound series are determined on a standard curve obtained by plotting time versus concentration using the Pharmacokinetic software DAS 3.0, and the elimination half-life ($t_{1/2}$) was determined from the concentration-time plots.

3. Experimental Results

TABLE 3

| | Metabolic stability ($t_{1/2}$) of MTB compound series measured in human liver microsomes | | | |
|---|---|---|---|---|
| | Potassium Butylphthalide | BZP | Compound 14 | Compound 15 | Compound 17 |
| $t_{1/2}$(h) | <1 | 4.17 | 2.44 | 19.09 | 19.30 |

The results show that the compounds 15 and 17 respectively have a longer elimination half-life ($t_{1/2}$) in the human liver microsomes of 19.09 hours and 19.30 hours relative to potassium butylphthalide and BZP, wherein potassium butylphthalide has a half-life of less than 1 hour and BZP has a half-life of 4.17 hours.

EXAMPLE 11

Acute Toxicity on Mice

The drugs were diluted in the water to prepare different concentration ranges per each drug, and injected via tail vein into the mice, respectively. Mortality was determined and LD50 (median lethal dose) value was calculated. The results are shown in Table 4.

TABLE 4

| | LD50 of MTB compound series | | | |
|---|---|---|---|---|
| | Potassium Butylphthalide | BZP | Compound 15 | Compound 17 |
| T½ (h) | 373 mg/kg | 330 mg/kg | 1036 mg/kg | 1100 mg/kg |

The result shows that the compound 15 and the compound 17 show similar toxicity, but are significantly less toxic than potassium butylphthalide and BZP.

It will be obvious to those skilled in the art that changes and modifications may be made, and therefore, the aim in the appended claims is to cover all such changes and modifications.

What is claimed is:

1. A compound of formula II:

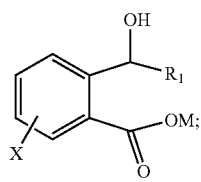

II wherein:
X represents a mono substituent on a benzene ring, and is selected from the group consisting of —H, —I, —Br, —Cl, —F, —CN, and an amino;
$R_1$ is $C_{2-10}$ alkyl substituted by cyclopropane or fluorine; and
M is an amine ion or a metal ion.

2. The compound of claim 1, wherein:
X represents a mono substituent on a benzene ring, and is selected from the group consisting of —H, —I, —Br, —Cl, —F, —CN, and an amino;
$R_1$ is $C_{3-5}$ alkyl substituted by cyclopropane or fluorine; and
M is an ion of K, Na, Ca, Zn or Mg.

3. The compound of claim 1, wherein X is Br or F; $R_1$ is $C_{3-5}$ alkyl substituted by cyclopropane or fluorine; and M is an ion of K, Na, or Ca.

4. The compound of claim 3, wherein $R_1$ has one of the following structural formulas:

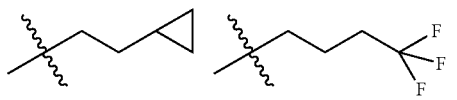

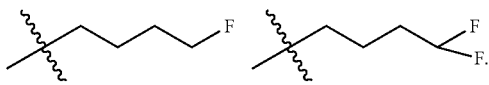

5. The compound of claim 1, wherein the compound has one of the following structural formulas:

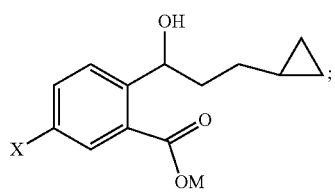

IV

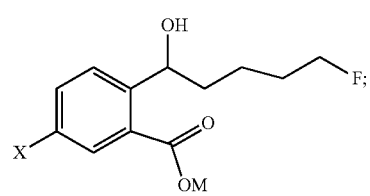

VI

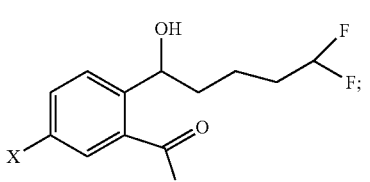

VIII

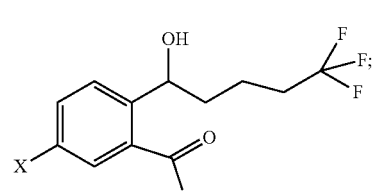

X wherein:
M is an ion of K, Na, Ca, Zn or Mg, and X is Br or F.

6. The compound of claim 5, wherein the compound is one of the following compounds:
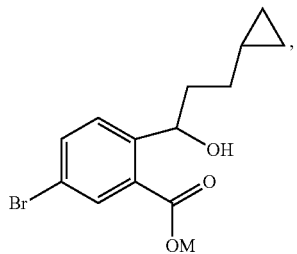
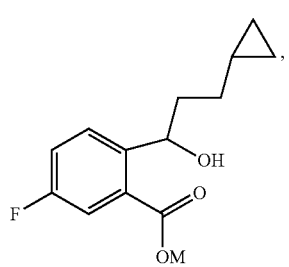
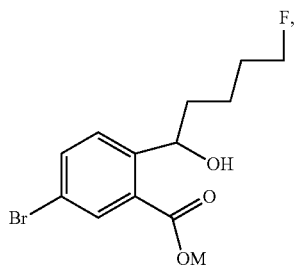
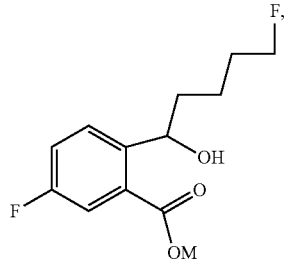
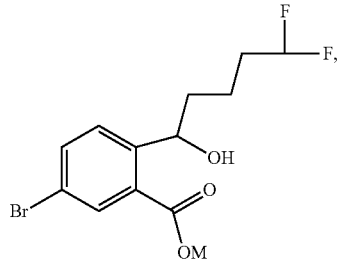
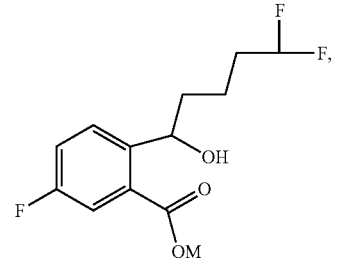
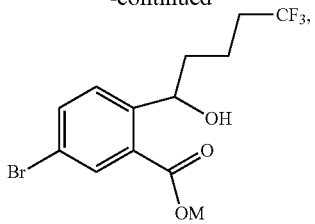
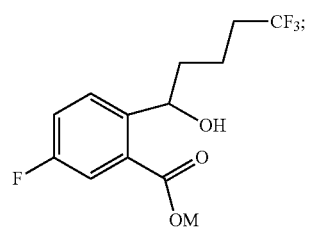
and M is an ion of K, Na, Ca, Zn or Mg.
7. The compound of claim 1, wherein the compound is one of the following compounds:
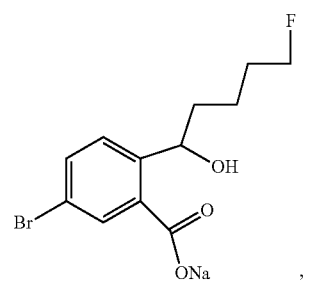
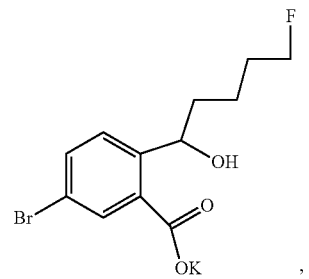
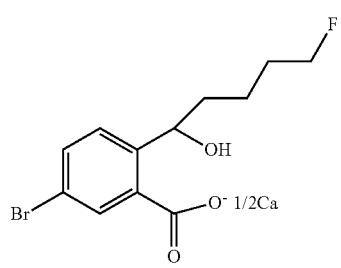

8. The compound of claim 7, wherein a crystal of the compound 17 is polymorphic form A; under a Cu-Kα line, λ=1.5418 Å, an X-ray powder diffraction of the polymorphic form A under an diffraction angle 2θ is 6.10, 8.43, 10.36, 12.18, 13.34, 14.46, 15.30, 16.77, 17.93, 18.31, 18.60, 19.36, 20.16, 20.88, 21.30, 21.70, 22.10, 22.81, 23.18, 23.57, 24.37; a characteristic peak occurs at 6.88, and an error range of the diffraction angle 2θ is ±0.2.

* * * * *